US009271952B2

(12) United States Patent
Cushing

(10) Patent No.: US 9,271,952 B2
(45) Date of Patent: Mar. 1, 2016

(54) COMPOSITIONS AND METHODS FOR TREATING NEPHROPATHY

(71) Applicant: Complexa, Inc., Pittsburgh, PA (US)

(72) Inventor: Daniel Joseph Cushing, Phoenixville, PA (US)

(73) Assignee: Complexa, Inc., Pittsburgh, PA (US)

( * ) Notice: Subject to any disclaimer, the term of this patent is extended or adjusted under 35 U.S.C. 154(b) by 0 days.

(21) Appl. No.: 13/649,077

(22) Filed: Oct. 10, 2012

(65) Prior Publication Data

US 2013/0101514 A1 Apr. 25, 2013

Related U.S. Application Data

(60) Provisional application No. 61/545,834, filed on Oct. 11, 2011.

(51) Int. Cl.

| | | |
|---|---|---|
| *A61K 9/42* | (2006.01) | |
| *A61K 31/201* | (2006.01) | |
| *C07H 13/06* | (2006.01) | |
| *A61K 33/24* | (2006.01) | |
| *A61K 45/06* | (2006.01) | |
| *A61N 5/10* | (2006.01) | |
| *A61K 49/04* | (2006.01) | |
| *A61K 49/10* | (2006.01) | |
| *A61K 31/202* | (2006.01) | |
| *A61K 31/401* | (2006.01) | |
| *A61K 31/4184* | (2006.01) | |

(52) U.S. Cl.
CPC .......... *A61K 31/201* (2013.01); *A61K 31/202* (2013.01); *A61K 31/401* (2013.01); *A61K 31/4184* (2013.01); *A61K 33/24* (2013.01); *A61K 45/06* (2013.01); *A61K 49/0438* (2013.01); *A61K 49/103* (2013.01); *A61K 49/106* (2013.01); *A61N 5/10* (2013.01); *C07H 13/06* (2013.01)

(58) Field of Classification Search
CPC ..... A61K 31/201; A61K 45/06; A61K 33/24; C07H 13/06
See application file for complete search history.

(56) References Cited

U.S. PATENT DOCUMENTS

| 4,599,430 | A | 7/1986 | Milberger | 548/548 |
|---|---|---|---|---|
| 6,346,231 | B1 | 2/2002 | Opheim | 424/45 |
| 6,652,879 | B2 | 11/2003 | Opheim | 424/45 |
| 2007/0232579 | A1 | 10/2007 | Freeman et al. | 514/568 |
| 2011/0196037 | A1 | 8/2011 | Yang | 514/560 |

FOREIGN PATENT DOCUMENTS

| WO | WO 2005/110396 | 11/2005 | A61K 31/21 |
|---|---|---|---|
| WO | WO 2009/149496 | 12/2009 | A61P 9/10 |
| WO | Wo-2009/155439 A2 * | 12/2009 | |
| WO | WO 2010/432877 | 4/2010 | C07D 345/00 |
| WO | WO 2010/078504 | 7/2010 | A01N 25/26 |
| WO | WO 2010/012777 | 11/2010 | A61K 8/18 |

OTHER PUBLICATIONS

Liu et al., Nitro-oleic acid protects the mouse kidney from ischemia and reperfusion injury, Aug. 27, 2008, American Journal of Physiology Renal Physiology, pp. F942-F949.*
Rudnick et al., Contrast-induced nephropathy: How it develops, how to prevent it, Jan. 2006, Cleveland Clinic Journal of Medicine, vol. 73 No. 1, pp. 75-87.*
Hartmann et al., A randomized trial comparing the nephrotoxicity of cisplatin/ifosfamide-based combination chemotherapy with or without amifostine in patients with solid tumors, 2000, Investigational New Drugs, vol. 18, pp. 281-289.*
Morgan et al., Use of Animal Models of Human Disease for Nonclinical Safety Assessment of Novel Pharmaceuticals, Sep. 11, 2012, Toxicologic Pathology, vol. 00, pp. 1-11.*
Khoo et al., "Activation of vascular endothelial nitric oxide sythase and heme oxygenase-1 expression by electrophilic nitro-fatty acids", published Oct. 24, 2009, Free Radical Biology & Medicine, vol. 48, pp. 230-239.*
Adjei, A.A., et al., "Cancer Research" 60: 1871-1877 (2000).
Banker, Gilbert S. and Rhodes, Christopher T., "Modern Pharmaceutics" *Marcel Dekker, Inc.* (1979).
Blakemore, P.R., "The modified Julia olefination: alkene synthesis via the condensation of metallated heteroarylalkylsufones with carbonyl compounds" *J. Chem. Soc., Perkin Trans.* 1: 2563-2585 (2002).
Boruwa, J., "Catalytic Asymmetric Henry Reaction" *Tetrahedron: Asymmetry* 17: 3315-3326 (2006).
de Meijere, A. and Diedrich, F., "Metal-Catalyzed Cross-Coupling Reactions vol. 1" *Wiley-VCH Verlag GmbH & Co.* (2004).
de Meijere, A. and Diedrich, F., "Metal-Catalyzed Cross-Coupling Reactions vol. 2" *Wiley-VCH Verlag GmbH & Co.* (2004).
Gennaro, Alfonso R., "Remingtons' Pharmaceutical Sciences" *Mack Pub Co., 18th Ed.* (1990).
Goodman and Gilman's: The Pharmacological Basis of Therapeutics, 10th edition, MacMillan Publishing Co., New York (2001).
Goodman and Gilman's: The Pharmacological Basis of Therapeutics, 6th edition, MacMillan Publishing Co., New York (1980).
Goodman and Gilman's: The Pharmacological Basis of Therapeutics, 9th edition, MacMillan Publishing Co., New York (1996).
International Search Report issued in corresponding PCT application, PCT/US2012/059722, pp. 1-6 (Aug. 19, 2013).
Karp, J.E., et al., "Blood" 97(11): 3361-3369 (2001).
Luzzio, F.A., "The Henry reaction: recent examples" *Tetrahedron* 57: 915-945 (2001).
Rowe, R.C. and Shesky, P.J., "Handbook of Pharmaceutical Excipients" *Pharmaceutical Press, Fifth Edition* (2006).
Wang, Haiping, "Nitro-oleic acid protects against endotoxin-induced endotoxemia and multiorgan injury in mice" *Am J Physiol Renal Physiol* 298: F754-F762 (2010).

(Continued)

*Primary Examiner* — Ali Soroush
(74) *Attorney, Agent, or Firm* — Pepper Hamilton LLP

(57) ABSTRACT

Activated fatty acids, pharmaceutical composition compositions including activated fatty acids, methods for using activated fatty acids to treat nephropathy, and methods for preparing activated fatty acids are provided herein.

28 Claims, No Drawings

(56) References Cited

OTHER PUBLICATIONS

Woodcock, S.R., "Synthesis of Nitrolipids. All Four Possible Diastereomers of Nitrooleic Acids: €- and (Z)-, 9- and 10-Nitro-octadec-9-enoic Acids" *Organic Letters* 8: 3931-3934 (2006).

Written Opinion issued in corresponding PCT application, PCT/US2012/059722, pp. 1-8 (Aug. 19, 2013).
European Search Report issued in corresponding foreign application, pp. 1-6 (Feb. 2, 2015).
International Preliminary Report on Patentability issued in corresponding foreign application, pp. 1-9 (Apr. 24, 2014).

* cited by examiner

COMPOSITIONS AND METHODS FOR TREATING NEPHROPATHY

CROSS-REFERENCE TO RELATED APPLICATIONS

The present application claims priority from U.S. Provisional Patent Application Ser. No. 61/545,834, filed Oct. 11, 2011, which is hereby incorporated in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Summary of the Invention

Embodiments of the invention are directed to a pharmaceutical composition and methods for treating kidney injury or disease and, in particular, pharmaceutical compositions and methods for treating kidney injury, kidney disease, hypoperfusion of the kidney from any cause, alterations in instrinsic renal function, or to functional abnormalities in the urinary tract encompassing prerenal, intrinsic and postrenal causes of renal dysfunction. The compositions of such embodiments include at least one activated fatty acid and a pharmaceutically effective carrier, diluent, excipient, or combination thereof, and in some embodiments, the at least one activated fatty acid may be combined with additional forms of treatment either in a single pharmaceutical composition or as part of a multi-component treatment regimen. The methods of various embodiments include administering an effective amount of any of these pharmaceutical composition to a patient in need of treatment.

DESCRIPTION OF DRAWINGS

Not applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer an agent to a patient, whereby the agent positively impacts the tissue to which it is targeted. Thus, as used herein, the term "administering," when used in conjunction with a nitrated lipid can include, but is not limited to, providing a nitrated lipid to a subject systemically by, for example, intravenous injection, whereby the agent reaches the target tissue. "Administering" a composition may be accomplished by, for example, injection, oral administration, topical administration, or by these methods in combination with other known techniques. Such combination techniques include heating, radiation, ultrasound and the use of delivery agents.

The term "animal" as used herein includes, but is not limited to, humans and non-human vertebrates such as wild, domestic, and farm animals.

The term "improves" is used to convey that the present invention changes either the characteristics and/or the physical attributes of the tissue to which it is being provided, applied, or administered. The term "improves" may also be used in conjunction with a diseased state such that when a diseased state is "improved" the symptoms or physical characteristics associated with the diseased state are diminished, reduced, or eliminated.

The term "inhibiting" includes the administration of a compound of the present invention to prevent the onset of the symptoms, alleviating the symptoms, or eliminating the disease, condition, or disorder.

By "pharmaceutically acceptable" it is meant the carrier, diluent or excipient must be compatible with the other ingredients of the formulation and not deleterious to the recipient thereof.

"Pharmaceutical composition" as used herein generally refers to natural, bioactive chemical compounds that provide physiological benefits, including disease prevention and health promotion which may be used to supplement the diet. Pharmaceutical compositions can be either purified or concentrated by using bioengineering methods and can be enhanced through genetic methods, which contain elevated levels of natural substances. Examples of pharmaceutical compositions include isolated nutrients and herbal products and generally contain at least one of the following ingredients: a vitamin, a mineral, an herb or other botanical, an amino acid, a metabolite, constituent, extract, or combination of these ingredients. Common examples of pharmaceutical compositions include beta-carotene, ephedra, ginko biloba, goldenseal, valerian, ginseng, green tea extract, and echinacea. The pharmaceutical compositions described herein may be useful for maintenance and support of, for example, healthy joints, skin, eye, and brain function, heart and circulatory system, and general health.

As used herein, the term "agent," "active agent," "therapeutic agent," or "therapeutic" means a compound or composition utilized to treat, combat, ameliorate, prevent or improve an unwanted condition or disease of a patient. In part, embodiments of the present invention are directed to affecting of inflammation, obesity, obesity-related diseases, metabolic diseases, cardiovascular and heart related diseases, cerebrovascular, kidney disease, and neurodegenerative diseases, cognitive disorders, cancer or the aberrant proliferation of cells, and the like.

A "therapeutically effective amount" or "effective amount" of a composition is a predetermined amount calculated to achieve the desired effect, e.g., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder.

The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes eliciting a clinically significant response without excessive levels of side effects. Treatment also includes prolonging survival as compared to expected survival if not receiving treatment.

As used herein and in the attached claims, the term "enriched" shall mean that the composition or portion of the composition includes a concentration of the identified component that is greater than the amount of the component naturally occurring in the composition. For example, with reference to activated fatty acids, a composition enriched for activated fatty acids may include greater than at least 50 nM activated fatty acids. Therefore, a composition that is enriched for activated fatty acids may be at least 0.05% by weight activated fatty acid, at least 0.1% by weight activated fatty acid, at least 0.15% by weight activated fatty acid, at least 0.25% by weight activated fatty acid, at least 0.5% by weight activated fatty acid, at least 1.0% by weight activated fatty acid, at least 2% by weight activated fatty acid, and so on.

The kidney is highly susceptible to toxic injury by antineoplastic agents, antibiotics, radiation, analgesics, nonsteroidal anti-inflammatory drugs, angiotensin-converting enzyme inhibitors, and contrast media, or other substances used to enhance the contrast of structures or fluids within the body during medical imaging, used to diagnose, identify or treat a medical condition in a human or other mammal. As a result, patients frequently suffer from kidney injury that can interrupt or inhibit one or more functions of the kidney such as, but not limited to, regulating water, electrolyte and acid-base balance, excreting of metabolic wastes, excreting bioactive substances, including administered drugs and imaging agents, detoxifying and excreting environmental toxins, regulating of arterial blood pressure, regulating of red blood cell production and Vitamin D synthesis, and gluconeogenesis. Many of these patients, therefore, suffer from nephrotoxicity, hypercalcemia, hyperuricemia, lysozymuria, microangiopathic hemolysis, disseminated intravascular coagulopathy, immune complex-mediated glomerulopathy, paraprotein-related nephropathy, amyloidosis, or minimal-change nephritis and urinary tract infections. Failure of renal function, either acute or chronic, results in fluid, electrolyte and acid-base imbalances, alterations in excretion of metabolic wastes, and accumulation of administered therapeutic agents as well as environmental toxins. Acute renal failure may be described as pre-renal causes, kidney failure resulting from inadequate blood flow to the kidney and resulting in intravascular volume depletion, structural lesions of the renal arteries, drug effects on renal blood flow, and hypotension from any cause that results in renal hypoperfusion, intrinsic causes, kidney disorders that result in damage to the tubules, glomeruli, interstitium, and/or vascular tissues within the kidney directly rather than indirectly as a secondary consequence of inadequate perfusion or obstruction, and postrenal causes, kidney disease related to urinary tract obstruction, from either kidney stones, structural lesions (e.g. tumors, prostatic hyperplasia, or strictures), or functional abnormalities (e.g. spasm, or effects of administered agents).

Recent studies suggest that nitro fatty acids such as 9- or 10-nitro octadecenoic acid ("nitro oleic acid") and the various regioisomers (9-, 10-, 12- and 13-nitro) of nitro linoleic acid are adaptive mediators that play a crucial role in linking disease processes with underlying cellular events, including those in the kidney.

Embodiments of the invention are directed to a pharmaceutical composition and methods for treating kidney injury or disease and, in particular, pharmaceutical compositions and methods for treating kidney injury, kidney disease, hypoperfusion of the kidney from any cause, alterations in instrinsic renal function, or to functional abnormalities in the urinary tract encompassing prerenal, intrinsic and postrenal causes of renal dysfunction as described above. The compositions of such embodiments include at least one activated fatty acid and a pharmaceutically effective carrier, diluent, excipient, or combination thereof, and in some embodiments, the at least one activated fatty acid may be combined with additional forms of treatment either in a single pharmaceutical composition or as part of a multi-component treatment regimen. The methods of various embodiments include administering an effective amount of any of these pharmaceutical composition to a patient in need of treatment.

In the methods of various embodiments, pharmaceutical compositions including at least one activated fatty acid can be administered to a subject in an "effective amount." An effective amount may be any amount that provides a beneficial effect to the patient, and in particular embodiments, the effective amount is an amount may 1) prevent the subject from experiencing one or more adverse effects associated with a administered agents, such as those used to diagnose, identify, and treat medical conditions, 2) reduce side effects experienced by the subject as a result of a medical therapy or reduce the side effects known to result from such therapies, and/or 3) eliminate side effects resulting from a medical treatment experienced by the subject prior to administration of the activated fatty acids or eliminate the side effects known to result from such treatment. In some embodiments, the side effects may include general injury or damage to the urinary tract and injury or damage to one or more kidney. The urinary tract or kidney injury or damage may manifest as drug-induced nephropathy, radiation-induced nephropathy, contrast agent-induced nephropathy, microangiopathic hemolysis, minimal-change nephritis, and other diseases related to diagnostic and therapeutic maneuvers such as, but not limited to, hypercalcemia, hyperuricemia, lysozymuria, disseminated intravascular coagulopathy, immune complex-mediated glomerulopathy, paraprotein-related nephropathy, amyloidosis, and urinary tract infections or any combinations of these injuries or diseases. Such treatment may, generally, result in improved or increased renal function, avoidance of further deterioration of renal function, avoidance of renal replacement therapy such as intermittent hemodialysis, or continuous renal replacement therapies, shortened hospital stays, and the benefits deriving therefrom, and general improvement in the health and well-being of the patient being treated.

These side effects associated with the medical treatments identified above are generally readily apparent, and patients in need of treatment can be easily identified. In embodiments in which pharmaceutical compositions are used to treat organ damage patients having organ damage can be identified using well-known pathological techniques. For example, in some embodiments, kidney damage may be identified by examining renal morphology, observing dilation of renal tubules, and the appearance of protein cast. In other embodiments, organ damage, such as kidney injury or damage may be identified by measuring biomarkers associated with such organ damage including, but are not limited to, biomarkers associated with organ dysfunction, oxidative stress, necrosis, apoptosis, or a combination thereof. Examples of biomarkers associated with organ dysfunction include, but is not limited to, plasma creatinine, blood urea nitrogen (BUN), serum aspartate aminotransferase (AST), and alanine aminotransferase (ALT), nicotinamide adenine dinucleotide phosphate (NADPH) oxidase, $p47^{phox}$ and $gp91^{phox}$, thiobarbituric acid-reactive substances (TBARS), caspase 3, caspase 6, and caspase 9, myeloperoxidase (MPO), and combinations thereof. Therefore, renal injury can be detected by, for example, increased serum creatinine levels, increased serum and urinary neutrophil gelatinase-associated lipocalin (NGAL), increased urinary IL-18, increased plasma IL-6 or cystatin C, increased urinary kidney molecule 1 (KIM-1), increased urinary protein excretion, alterations in urinary flow, either oliguria or polyuria, changes in the fractional excretion of sodium or other markers of organ dysfunction, oxidative stress, necrosis apoptosis or a combination thereof.

A specific effective amounts of the pharmaceutical composition including an activated fatty acid may vary depending upon factors including, for example, the condition treated, the age, body weight, general health, sex, and diet of the subject, dose intervals, administration route, and the like and combinations thereof. In some exemplary embodiments, an effective amount of the activated fatty acid provided in a pharmaceutical composition and ranges from about 1 µg per day to about 1 g per day, from about 1 mg per day to about 500 mg per day, from about 1 mg per day to about 100 mg per day, from about 2 mg per day to about 10 mg per day, or any amount in between these ranges or identified below.

The methods of embodiments include administering the pharmaceutical compositions to a subject via any administration routes and encompass various pharmaceutical formulations that allow for such administration routes. For example, the formulations of various embodiments can be granules, powders, tablets, capsules, syrup, suppositories, injections, emulsions, elixirs, suspensions, or solutions, and these formulations may be delivered to the subject by various routes of administration including, but not limited to, topical administration, transdermal administration, oral administration, nasal administration, rectal administration, subcutaneous injection, intravenous injection, intramuscular injection, or intraperitoneal injection. In other embodiments, the activated fatty acids describe herein can be incorporated into a food product such as, but are not limited to, butter, margarine, vegetable oils, and the like. Various formulations, delivery methods, and pharmaceutically acceptable diluents, carriers, and excipients are described in U.S. Publication No. 2007/0232579, which is hereby incorporated by reference in its entirety.

The methods of embodiments encompassed by the invention may be used to reduce or eliminate side effects associated with any medical therapies and diagnostic agents, and in particular embodiments, the medical therapies and diagnostic agent administration that may be a therapy that is capable of producing toxicity in normal tissues. Such medical therapies may include the use of chemical agents, physical agents, or a combination thereof. For example, in some embodiments, the methods described herein may be used to reduce or eliminate side effects associated with chemical agents including, but are not limited to, alkylating agents, anti-metabolites such as, but are not limited to, azathioprine, mercaptopurine, and other purine and pyrimidine analogues, alkaloids and terpenes such as, but are not limited to, vinca alkaloids, etoposide, teniposide, paclitaxel, and docetaxel, topoisomerase inhibitors such as, but are not limited to, irinotecan, topotecan, and amsacrine, antibiotics, monoclonal antibodies such as, but are not limited to, trastuzumab, cetuximab, rituximab, and bevacizumab, tyrosine kinase inhibitors, hormones such as, but are not limited to, steroids such as dexamethasone, finasteride, aromatase inhibitors, tamoxifen, and goserelin, and the like and combinations thereof. In particular embodiments, the methods described herein may be employed to reduce the side effects associated with alkylating agents such as, but are not limited to, cisplatin, mechlorethamine, cyclophosphamide, chlorambucil, carboplatin, oxaliplatin, and the like, which are known to have a particularly detrimental effect of the kidneys and urinary tract, and in still other embodiments, the methods described herein may be used to reduce or eliminate adverse effects of contrast agents, such as, but not limited to, diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, calcium iopodate, ethyl esters of iodised fatty acids, iopydol, propyliodone, iofendylate, lipiodol, and gadolinium-based agents such as, but not limited to gadobenic acid, gadobutrol, gadodiamide, gadofosveset, gadolinium, gadopentetic acid, gadoteric acid, gadoteridol, gadoversetamide, gadoxetic acid, and other contrast agents currently used in X-ray, CT, and MRI. Other chemical agents whose side effects are encompassed be the methods of various embodiments include, but are not limited to, contrast agents, non-steroidal anti-inflammatory drugs NSAIDs, cyclooxygenase-II (COX-2) inhibitors, angiotensin-converting enzyme (ACE) inhibitors, angiotensin II receptor blockers (ARBs), lithium, and the like and combinations thereof. Physical agents whose side effects can be reduced or eliminated by administering a pharmaceutical composition including at least one activated fatty acid include, but is not limited to, radiation including ionizing radiation and laser radiation.

In particular embodiments, activated fatty acids may be administered to counteract the adverse effects of administration of contrast agents. Various contrast agents are known and used in the medical arts, and these agents are known to cause various kidney related maladies often referred to as contrast agent induced nephropathy (CIN). CIN is thought to result from vasoconstriction resulting from the relatively high osmolality, exhibited by commonly used contrast agents. For example, contrast agents commonly exhibit osmolalities of from about 1800 mosmol/kg to about 290 mosmol/kg. Without wishing to be bound by theory, administration of activated fatty acids can reduce vasoconstriction associated with contrast agent administration thereby counteracting the effects of contrast agent administration.

Embodiments of the invention are, therefore, directed to methods for reducing vasoconstriction by administering at least one activated fatty acid. Certain embodiments include methods for reducing vasoconstriction resulting from administration of agents having an osmolality of up to about 2000 mosmol/kg and, in some embodiments, from 1800 mosmol/kg to about 290 mosmol/kg, or from about 1800 mosmol/kg to about 500 mosmol/kg. In particular embodiments, the agent may be a contrast agent such as, for example, diatrizoic acid, iopamidol, iodixanol, iohexol, ioxaglic acid, ioversol, iopromide, iothalamic acid, and the like and combinations thereof.

Other embodiments are directed to methods for reducing kidney damage or injury as a result of administration of a compound that accumulates in the kidneys reducing the glomerular filtration rate. For example, compounds such as cisplatin include a heavy metal atom, platinum, that can accumulate in the kidneys and, more specifically, in the proximal tubules of the kidney, reducing the glomerular filtration rate and inducing tubule epithelial cell toxicity, vasoconstriction, and inflammation. This accumlulation can be characterized as causing the concentration of the heavy metal component of the agent to have a concentration in the kidney that is up to about 10 times greater than in other organs, and in some embodiments, the concentration of heavy metal in the kidney may be from about 1.5 times to about 5.0 times greater or about 2 times to about 4 times that of other organs. Thus, in particular embodiments, at least one activated fatty acid may be administered to reduce tubule epithelial cell toxicity and inflammation and/or the reduction in glomerular filtration rate associated with administration of heavy metal containing agents such as, for example, cisplatin, carboplatin, oxaliplatin, and the like and combinations thereof. In some embodiments, administration of the heavy metal containing agent may cause the concentration of heavy metal to be up to about 10 times greater than in other organs, and in other embodiments, administration of the heavy metal containing active agent may cause the heavy metal concentration in the kidney may be from about 1.5 times to about 5.0 times greater or about 2 times to about 4 times that of other organs.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the activated fatty acids and at least one therapeutic agent either before or after the other. A variety of therapeutic agents may be combined with the at least one activated fatty acid used including, but not limited to, those useful in the treatment of the underlying condition, disease, or disorder giving rise to any of the toxic medical therapies disclosed herein. In some embodiments, the at least one activated fatty acid may be combined with a chemotherapeutic agent or contrast agent in a single pharmaceutical composition to allow the chemotherapeutic agent or contrast agent and the activated fatty acid to be delivered simultaneously. For example, in certain embodiments, a contrast agent such as iopamidol may be combined with an activated fatty acid such as nitro-linoleic acid, nitro-oleic acid, or a combination thereof and this composition may be delivered to a patient.

In various embodiments, the at least one activated fatty acids may include any unsaturated or polyunsaturated fatty acid having one or more electron withdrawing group wherein at least one electron withdrawing group is associated with a carbon-carbon double bond or a heteroatom or a pharmaceutically acceptable salt thereof. In some embodiments, the unsaturated or polyunsaturated fatty acid may include an aliphatic chain having a number of carbons from about 4 to about 25, and in other embodiments, the unsaturated or polyunsaturated fatty acid may include an aliphatic chain having 4 to 23 carbons or, in certain embodiments, an aliphatic chain having 4, 5, 6, 7, 8, 9, 10 11, 12, 13, 14, 15, 16, 17, 18, 19, 20, 21, 22, 23, 24, or 25 carbons. In additional embodiments, unsaturated or polyunsaturated fatty acid may be a glycolipid, a glycerolipid, a phospholipid, or a cholesterol ester.

The one or more electron withdrawing group of various embodiments may include, but are not limited to, aldehyde (—COH), acyl (—COR), carbonyl (—CO), carboxylic acid (—COOH), ester (—COOR), halides (—Cl, —F, —Br, —I), fluoromethyl (—CF$_n$, n=1-3), allyl fluoride (—CH=CHCH$_2$F), cyano (—CN), sulfoxide (—SOR), sulfonyl (—SO$_2$R), sulfonic acid (—SO$_3$H), 1°, 2° and 3° ammonium (—NR$_3^+$), or nitro (—NO$_2$), wherein R is a hydrogen, methyl or C$_2$-C$_6$ alkyl, and in particular embodiments, the one or more electron withdrawing group may be a nitro (—NO$_2$) group. In some embodiments, the one or more electron withdrawing group may be positioned on an alpha carbon of a carbon-carbon double bond of the unsaturated or polyunsaturated fatty acid, and in other embodiments, the one or more electron withdrawing group may be positioned on a beta carbon of a carbon-carbon double bond of the unsaturated or polyunsaturated fatty acid. In still other embodiments, the one or more electron withdrawing group may be positioned on a gamma carbon of a carbon-carbon double bond of the unsaturated or polyunsaturated fatty acid. Thus, the one or more electron withdrawing group may be an electron withdrawing vinyl group or an electron withdrawing allylic group.

A carbon-carbon double bond may occur at any carbon of the aliphatic chain of the unsaturated or polyunsaturated fatty acid. For example, in some embodiments, the unsaturated or polyunsaturated fatty acid may be a fatty acid with two or more conjugated carbon-carbon double bonds, and in particular embodiments, at least one of the one or more electron withdrawing group may be at any carbon in the two or more conjugated carbon-carbon double bonds. In certain embodiments, at least one of the one or more electron withdrawing group may be positioned at C-9, C-10, C-12, C-13 or a combination thereof. Carbon-carbon double bonds that are associated with the one or more electron withdrawing group may be in cis or trans configuration, and the one or more electron withdrawing group may be in an absolute stereochemistry of R at an $sp^3$ chiral/stereogenic or S at an $sp^3$ chiral/stereogenic center.

In some embodiments, one or more heteroatoms may be positioned anywhere on the aliphatic chain of the unsaturated or polyunsaturated fatty acid, and in particular embodiments, at least one heteroatom may be positioned at the first 1, 2, 3, or 4 carbons from the carboxy terminus of the fatty acid to produce a carbonate, acetic acid, propionic acid, or butanoic acid derivatives of the activated fatty acid. In other embodiments, an electron withdrawing group may be positioned at a carbon immediately adjacent to the heteroatom, or in further embodiments, the carbon immediately adjacent to the carbon immediately adjacent to the heteroatom. In still other embodiments, an electron withdrawing group may be positioned at both carbons immediately adjacent to the heteroatom, and/or the carbon immediately adjacent to the carbon immediately adjacent to the heteroatom. In yet other embodiments, there may be no electron withdrawing associated with the heteroatom provided that the aliphatic chain include at least one electron withdrawing group associated with another heteroatom or a carbon-carbon double bond.

In some embodiments, one or more non-carbon-carbon linkage such as, for example, an ester linkage, an ether linkage, and a vinyl ether linkage may be substituted on the aliphatic chain of the unsaturated or polyunsaturated fatty acid, and in other embodiments, the unsaturated or polyunsaturated fatty acid may further include one or more functional group other than an electron withdrawing group positioned at any carbon of the aliphatic chain of the unsaturated or polyunsaturated fatty acid.

In particular embodiments, the activated fatty acids may be activated oleic acid or activated linoleic acid or a combination thereof, and in certain embodiments, the activated fatty acids may be activated oleic acid. While embodiments are not limited by the electron withdrawing group associated with the activated oleic acid or linoleic acid of such embodiments, the electron withdrawing group, in some embodiments, may be a nitro group. In certain embodiments, the activated fatty acid is nitro-oleic acid (ocatadecac-9-enoic acid) having an electron withdrawing group at either C-13 or C-12.

In still other embodiments, the activated fatty acids may be metabolites of the activated fatty acids described above. For example, activated fatty acids that have been degraded by, for example, β-oxidation, or that have been prepared to mimic the structure of activated fatty acids that have been degraded by β-oxidation, may be provided in the pharmaceutical compositions of embodiments. In such embodiments, the metabolite activated fatty acids may be an unsaturated or polyunsaturated may include an aliphatic carbon chain of from about 4 to about 30 carbons. In some embodiments, the metabolites may include an aliphatic carbon chain of from about 4 to about 20 carbons and, in other embodiments, from about 10 to about 16 carbons. Without wishing to be bound by theory, the presence of β-oxidation products in blood plasma may have physiological implications. For example, short-chain metabolites of activated fatty acids may be less hydrophobic than the parent acid, yet these compounds preserve the molecular determinants that may be important for, for example, PPARγ binding. Additionally, the smaller size the activated fatty acid metabolic products may allow these metabolites to partition differ physiologically between the hydrophobic and hydrophilic compartments, which may alter the anatomic distribution, chemical reactivity, and pharmacological profiles of these compounds by altering their availability to cellular targets.

Isomeric and tautomeric forms of activated fatty acids of the invention as well as pharmaceutically acceptable cations, anions, acids, bases, and salts of these compounds are also encompassed by the invention. For example, pharmaceutically acceptable cations include metallic ions and organic ions. In some embodiments, metallic ions may include, but are not limited to, appropriate alkali metal (group Ia) salts, alkaline earth metal (group IIa) salts and other physiological acceptable metal ions. Exemplary ions can include aluminum, calcium, lithium, magnesium, potassium, sodium and zinc in their usual valences. In other embodiments, organic salts may include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine), and procaine. Exemplary pharmaceutically acceptable acids can include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids. All of the above salts can be prepared by those skilled in the art by conventional means from the corresponding compound of the present invention.

The activated fatty acids described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts, and other physiological acceptable metal ions. Exemplary ions include aluminum, calcium, lithium, magnesium, potassium, sodium, and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine), and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of activated fatty acids of the invention, as well as pharmaceutically acceptable salts of these compounds, are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric, and galacturonic acids.

Suitable pharmaceutically acceptable base addition salts used in connection with the activated fatty acids of the invention include metallic ion salts and organic ion salts. Exemplary metallic ion salts include, but are not limited to, appropriate alkali metal (group Ia) salts, alkaline earth metal (group IIa) salts, and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

In some embodiments, the activated fatty acids may be combined with one or more secondary agents. Examples of secondary agents may vary depending upon the therapeutic or diagnostic agent administered to the patient and include, but are not limited to, anti-nausea agents, anti-vomiting agents, anti-hypotension agents, anti-inflammatory agents, and the like. In particular embodiments, the secondary agent may be an anti-nephrotoxicity agent. Anti-nephrotoxicity agents are known in the art and include, for example, amifostine (Ethyol™) and 2-mercapto ethane sulfonate sodium which are FDA-approved cytoprotective agents generally used to prevent and mitigate chemotherapy associated adverse events. More specifically, amifostine has been approved to prevent cisplatin-induced nephrotoxicity. 2-mercapto ethane sulfonate sodium (Mesna™) is used prevent hemorrhagic toxicity to the uroepithelial tract (e.g., ureters, urethra and bladder) associated with the administration of oxazaphosphorine chemotherapy, particularly ifosphamide and cyclophosphamide. In other embodiments, the secondary agent may be one or more angiotensin II inhibitors such as irbesartan (Avapro) and losartan (Cozaar™), or one or more angiotensin converting enzyme (ACE™) inhibitors such as ramipril (Altace™), enalapril (Vasotec™), lisinopril (Zestril™ and Prinivil™), quinapril (Accupril™), benazepril (Lotensin™), captopril (Capoten™), fosinopril (Monopril™), trandolapril (Mavik™), moexipril (Univasc™), and perindopril (Aceon™) or combinations thereof. Other anti-nephrotoxicity agents can be found, for example, in the Physicians Desk Reference (PDR) and American Hospital Formulary Service (AHFS), each of which are hereby incorporated by reference in their entireties.

Various embodiments include pharmaceutical compositions including the activated fatty acids of embodiments and one or more secondary agents described above. In some embodiments, the activated fatty acids and one or more of the secondary agents may be administered in a separate unit doses such that the activated fatty acids and the one or more secondary agent are provided in separate pharmaceutical compositions. As such, a first individual pharmaceutical composition containing the activated fatty acid and one or more second individual pharmaceutical compositions containing one or more secondary diabetes treatment agent may be prepared and provided to the patient as part of a broader treatment regimen including administration of, for example, a chemotherapeutic agent. In such embodiments, the individual pharmaceutical compositions may be administered concurrently or at different times throughout the day in the same course of treatment either concurrently with or separately from the chemotherapeutic agent.

In further embodiments, the activated fatty acid and the one or more secondary diabetes therapeutic agents may be provided in the same unit dose. The course of treatment may therefore include concurrent administration of both the activated fatty acids and the one or more secondary diabetes agents by administration of a single pharmaceutical composition. In some embodiments, the course of treatment may include concurrent administration of a single pharmaceutical composition including both the activated fatty acids and the one or more secondary diabetes agents and supplemental administration of either the activated fatty acid or at least one of the one or more secondary diabetes treatment agents individually administered.

In still further embodiments, the activated fatty acid and the one or more secondary agents may be covalently bound to one another. In some embodiments, a covalent linkage between the activated fatty acid and the one or more secondary agents may be a single bond, and in other embodiments, the covalent linkage may or include any number of atoms tethering the activated fatty acid to the one or more secondary agent. As such, the linker may include one or more alkyl, alkene, or alkyne, each of which may be substituted with any number of functional groups. In still other embodiments, the linker may include one or more heteroatoms, cycloalkyl groups, or aryl groups.

An effective amount of an activated fatty acid delivered during each administration cycle of the pharmaceutical compositions may range from about 10 mg/m$^2$/day to about 1000 mg/m$^2$/day. In some embodiments, an effective amount may be about 20 mg/m$^2$/day to about 700 mg/m$^2$/day, and in other embodiments, an effective amount may be about 30 mg/m$^2$/day to about 600 mg/m$^2$/day. In particular embodiments, an effective amount may be about 50 mg/m$^2$/day, about 400 mg/m$^2$/day, about 500 mg/m$^2$/day, or about 600 mg/m$^2$/day. In yet other embodiments, an effective amount of an activated fatty acid may vary as treatment progresses or side effects associated with the chemotherapeutic agent become more apparent or subside. For example, a dosage regimen may be increased or decreased as treatment proceeds through administration cycles, or the daily dosage may increase or decrease throughout administration. In additional embodiments, greater than 1000 mg/m$^2$/day may be administered because even high doses of activated fatty acid are generally tolerable to the patient and may not produce undesired physiological effects.

In some embodiments, activated fatty acids administered may include up to at least 5% by weight, at least 10% by weight, at least 20% by weight, at least 30% by weight, at least 40% by weight, at least 50% by weight, at least 60% by weight at least 70% by weight, at least 80% by weight, at least 90% by weight, or at least 100% by weight of one or more species of activated fatty acid. In particular embodiments, a single species of activated fatty acid may make up at least 10% by weight, at least 20% by weight, at least 30% by weight, at least 50%, at least 60% by weight, at least 70% by weight, or at least 80% by weight of the total activated fatty acid administered, and in other embodiments, a single species of activated fatty acids may make up about 5% to about 100% by weight, about 25% to about 75% by weight, or about 40% to about 55% by weight of the fatty acids administered. In particular embodiments, the ratio of activated fatty acid to non-activated may be from about 99:1 to about 1:99, about 1:4 to about 4:1, about 1:3 to about 3:1, or about 1:2 to about 2:1.

For example, in some embodiments, the activated fatty acids may be prepared from one of EPA or DHA or a combination of EPA and DHA. The composition administered may include about 5% to about 100% by weight, about 25% to about 75% by weight, or about 30% to about 60% by weight activated EPA and/or activated DHA, and any remainder may be made up of non-activated EPA and/or DHA. In compositions containing both activated EPA and activated DHA, the activated EPA and activated DHA may be present in a weight ratio of from 99:1 to 1:99, 1:4 to 4:1, 1:3 to 3:1, 1:2 to 2:1, or 1:1. In compositions containing activated EPA and/or activated DHA as well as non-activated EPA and/or DHA, the weight ratio of activated:non-activated may be from 99:1 to 1:99, 1:4 to 4:1, 1:3 to 3:1 or 1:2 to 2:1. In the embodiments described above, the percentage by weight may be based on the free acid or ester forms, although it is preferably based on the ethyl ester form of the ω-3 fatty acids even if other forms are utilized in accordance with the present invention.

In still other embodiments, the activated fatty acid may be prepared from a different base fatty acid than the non-activated fatty acids with which it is combined. For example, in some embodiments, the activated fatty acid may be an activated linoleic acid, an activated oleic acid, or combinations thereof, and these activated fatty acids may be combined with non-activated EPA and/or DHA. In such embodiments, the ratio of activated linoleic acid and/or activated oleic acid to non-activated EPA and/or DHA may be from about 99:1 to 1:99, 1:4 to 4:1, 1:3 to 3:1, 1:2 to 2:1, or 1:1. In particular embodiments, activated linoleic acid or oleic acid may be combined with EPA and DHA, and each of the three components may be provided in a ratio of from about 1:1:1, 2:1:1, 1:2:1, 1:1:2, 2:2:1, 1:2:2, 3:1:1, and the like.

In some embodiments, the pharmaceutical compositions including activated fatty acids may be combined with, for example, antioxidants, statins, squalene synthesis inhibitors, azetidinone-based compounds, low-density lipoprotein (LDL) catabolism activators, peroxisome proliferator-activated receptor (PPAR) antagonists or agonsits, antiarrhythmic agent, non-steroidal anti-inflammatory drugs (NSAIDs) and the like, and combinations thereof. In certain embodiments, the activated fatty acid may be combined with a peroxisome proliferator-activated receptor (PPAR) agonists and/or antagonists including, but are not limited to, for example, PPAR-alpha, PPAR-gamma, PPAR-delta, PPAR-beta, and combinations of two or more of these types. PPAR-alpha agonists include fibrate compounds, and are drugs that lower blood cholesterol levels by inhibiting the synthesis and secretion of triglycerides in the liver and activate a lipoprotein lipase. Examples of fibrate compounds include bezafibrate, beclobrate, binifibrate, ciplofibrate, clinofibrate, clofibrate, clofibric acid, etofibrate, fenofibrate, fenofibric acid, gemfibrozil, nicofibrate, pirifibrate, ronifibrate, simflbrate, theofibrate, and the like, and combinations thereof. PPAR-gamma agonists and/or antagonists include, for example, thiazolidinediones, pioglitazone, and rosiglitazone. PPAR-alpha/gamma agonists and/or antagonists include, for example, some non-thiazolidinediones, naviglitizar, and muraglitazar. PPAR agonists and/or antagonists active against all types of receptors (i.e., panagonists) may include, for example, netoglitazone.

In general, each of the one or more secondary agents may be provided in an appropriate amount based on the knowledge in the art, federal recommendations, and the like. The skilled artisan is therefore capable of determining an appropriate amount of any of the secondary agents described above. In some exemplary embodiments, the activated fatty acid may be combined with the one or more secondary agent in a range of about 1:1000 to about 1000:1 by weight or about 200:1 to about 200:1 by weight. In other exemplary embodiments, the activated fatty acid may be present in an amount from about 1 mg to about 3000 mg or from about 10 mg to about 2000 mg, and each of the one or more secondary agents may be present in an amount from about 1 mg to about 1000 mg, about 5 mg to about 500 mg, and about 5 mg to about 100 mg. In certain embodiments, a single dosage unit may include about 500 mg to about 2000 mg or about 1000 mg of one or more activated ω-3 fatty acids, and about 1 mg to about 50 mg or about 2 mg to about 25 mg of a amifostine or about 1 mg to about 30 mg or 2 to about 10 mg of an angiotension II or ACE inhibitor such as those provided.

The pharmaceutical compositions of the invention can be administered in any conventional manner by any route in which they are active. Administration can be systemic or local. For example, administration can be, but is not limited to, parenteral, subcutaneous, intravenous, intramuscular, intraperitoneal, transdermal, oral, buccal, ocular, intravaginally, or inhalation. In certain embodiments, the administration may be parenteral. In some embodiments, the pharmaceutical composition may be prepared in the presence or absence of stabilizing additives that favors extended systemic uptake, tissue half-life, and intracellular delivery. Thus, modes of administration for the compounds of the present invention (either alone or in combination with other pharmaceuticals) can be injectable (including short-acting, depot, implant, and pellet forms injected subcutaneously or intramuscularly). In some embodiments, an injectable formulation including an activated fatty acid may be deposited to a site of injury or inflammation, such as, for example, the activated fatty acid may be deposited directly in the kidney or another portion of the renal system.

Embodiments of the invention also include gel capsules containing activated fatty acids and, in some embodiments, one or more secondary agents and/or non-activated fatty acids and methods for preparing such gel capsules. The gel capsules of embodiments may be in soft or hard gel capsule form and may include any number of layers. For example, in some embodiments, the gel capsule may include one or more activated fatty acids encapsulated by a coating layer. In such embodiments, the one or more activated fatty acids may make up the core of the capsule and may generally be from about 10% by weight to about 95% by weight of the total gel capsule. However, in some embodiments, the core may be from about 40% by weight to about 90% by weight of the total weight of the capsule. In particular embodiments, the one or more activated fatty acids may be mixed with one or more stabilizers such as, for example, antioxidants, vitamin E, vitamin C, β-carotene, wheat germ oil and the like, and in some embodiments, the one or more activated fatty acid contained in the capsule may be combined with one or more solubilizers such as, for example, surfactants, hydrophilic or hydrophobic solvents, oils, or combinations thereof.

For example, in some embodiments a solubilizer may be vitamin E or a vitamin E derivative such as, but not limited to, α-, β-, γ-, δ-, ζ1-, ζ2- and ε-tocopherols, their dl, d and l forms and their structural analogues, such as tocotrienols; the corresponding derivatives, esters, produced with organic acids; and mixtures thereof. In particular embodiments, vitamin E derivative solubilizers may include tocopherols, tocotrienols, and tocopherol derivatives with organic acids such as acetic acid, propionic acid, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, polyethylene glycol succinate, and salicylic acid.

In other embodiments, monohydric alcohol including, for example, ethanol, isopropanol, t-butanol, a fatty alcohol, phenol, cresol, benzyl alcohol or a cycloalkyl alcohol, or monohydric alcohol esters of organic acids such as, for example, acetic acid, propionic acid, butyric acid, a fatty acid of 6-22 carbon atoms, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, and salicylic acid may be used as solubilizers. In certain embodiments, solubilizers in this group may include trialkyl citrates such as triethyl citrate, acetyltriethyl citrate, tributyl citrate, acetyltributyl citrate, and mixtures thereof; lower alcohol fatty acid esters such as ethyl oleate, ethyl linoleate, ethyl caprylate, ethyl caprate, isopropyl myristate, isopropyl palmitate and mixtures thereof and lactones ε-caprolactone, δ-valerolactone, β-butyrolactone, isomers thereof, and mixtures thereof.

In still other embodiments, the solubilizer may be a nitrogen-containing solvent such as, for example, acetonitrile, dimethylformamide, dimethylacetamide, N-alkylpyrrolidone, N-hydroxyalkylpyrrolidone, N-alkylpiperidone, N-alkylcaprolactam, and mixtures thereof wherein alkyl may be a $C_{1-12}$ branched or straight chain alkyl. In particular embodiments, nitrogen-containing solvents may include N-methyl 2-pyrrolidone, N-ethyl 2-pyrrolidone, or a mixture thereof. Alternatively, the nitrogen-containing solvent may be in the form of a polymer such as polyvinylpyrrolidone.

In yet other embodiments, solubilizers may include phospholipids such as phosphatidylcholine, phosphatidylethanolamine, phosphatidylserine, phosphatidylinositol, lecithins, lysolecithins, lysophosphatidylcholine, polyethylene glycolated phospholipids/liysophospholipids, lecithins/lysolecithins and mixtures thereof.

In still other embodiments, glycerol acetates and acetylated glycerol fatty acid esters and glycerol fatty acid esters may be used as solubilizers. In such embodiments, glycerol acetates may include acetin, diacetin, triacetin, and mixtures thereof. Acetylated glycerol fatty acid esters may include acetylated monoglycerides, acetylated diglycerides, and mixtures thereof with a fatty acid component that may be about 6 to about 22 carbon atoms. Glycerol fatty acid ester may be a monoglyceride, diglyceride, triglyceride, medium chain monoglycerides with fatty acids having about 6-12 carbons, medium chain diglycerides with fatty acids having about 6-12 carbons, medium chain triglycerides with fatty acids having about 6-12 carbons, and mixtures thereof.

Further embodiments include solubilizers that may be propylene glycol esters or ethylene glycol esters. In such embodiments, propylene glycol esters may include, for example, propylene carbonate, propylene glycol monoacetate, propylene glycol diacetate, propylene glycol fatty acid esters, acetylated propylene glycol fatty acid esters, and mixtures thereof. Alternatively, propylene glycol fatty acid esters may be a propylene glycol fatty acid monoester, propylene glycol fatty acid diester, or mixture thereof. In certain embodiments, propylene glycol ester may be propylene glycol monocaprylate, propylene glycol dicaprylate, propylene glycol dicaprate, propylene glycol dicaprylate/dicaprate, and mixtures thereof. Ethylene glycol esters may include monoethylene glycol monoacetates, diethylene glycol esters, polyethylene glycol esters, ethylene glycol monoacetates, ethylene glycol diacetates, ethylene glycol fatty acid monoesters, ethylene glycol fatty acid diesters, polyethylene glycol fatty acid monoesters, polyethylene glycol fatty acid diesters, and mixtures thereof. In such embodiments, the fatty acid may have about 6 to about 22 carbon atoms.

Hydrophilic solvents may also be utilized as solubilizers include, for example, alcohols, for example, water miscible alcohols, such as, ethanol or glycerol; glycols such as 1,2-propylene glycol; polyols such as a polyalkylene glycol, for example, polyethylene glycol. Alternatively, hydrophilic solvents may include N-alkylpyrolidones such as N-methylpyrrolidone, triethylcitrate, dimethylisosorbide, caprylic acid, or propylene carbonate.

The activated fatty acid containing core may be coated with one or more coating layer. For example, in some embodiments, the gel capsule may include a water-soluble gel layer between the coating layer and the activated fatty acid core. In other embodiments, the gel capsules may include a number of additional coatings on the capsules such as, for example, immediate release coatings, protective coatings, enteric or delayed release coatings, sustained release coatings, barrier coatings, and combinations thereof. In some embodiments, one or more secondary agent or non-activated fatty acid may be mixed with the activated fatty acid and/or be present in either a coating layer, a water-soluble gel layer, or an additional coating layer. Additionally, in various embodiments, the activated fatty acid and/or one or more secondary agents of the invention may be formulated with one or more additional non-pharmaceutically active ingredients including, but not limited to, solubilizers, antioxidants, chelating agents, buffers, emulsifiers, thickening agents, dispersants, and preservatives. In some embodiments, the activated fatty acids may be encapsulated in a coating prepared from gelatin as described in U.S. Pat. No. 6,531,150, which is hereby incorporated by reference in its entirety. The gelatin layer may further include one or more other non-gelatin protein and/or one or more polysaccharide such as, for example, albumin, pectin, guaran gum, carrageenan, agar, and the like, and/or one or more additive such as, for example, enteric materials, plasticizers, preservatives, and the like. Enteric materials used in embodiments of the invention include any material that does not dissolve in the stomach when the gel capsule is administered orally and include, but are not limited to, pectin, alginic acid, cellulose such as carboxyl methylcellulose, celluloseacetate phthalate, and the like, and Eudragit™, an acrylic copolymer. Without wishing to be bound by theory, the addition of an enteric coating may provide a means for masking the flavor of activated fatty acids by limiting the release of the activated fatty acids to the stomach. Plasticizers may include polyhydric alcohols, such as sorbitol, glycerin, polyethylene glycol, and the like. In the embodiments described above, each coating layer may be from about 0.001 to about 5.00 mm or 0.01 to 1.00 mm thick.

The coatings of various embodiment may further include one or more film forming materials and/or binders and/or other conventional additives such as lubricants, fillers, antiadherents, antioxidants, buffers, solubilizers, dyes, chelating agents, disintegrants, and/or absorption enhancers. Surfactants may act as both solubilizers and absorption enhancers. Additionally, coatings may be formulated for immediate release, delayed or enteric release, or sustained release in accordance with methods well known in the art. Conventional coating techniques are described, e.g., in Remington's Pharmaceutical Sciences, 18th Ed. (1990), hereby incorporated by reference. Additional coatings to be employed in accordance with the invention may include, but are not limited to, for example, one or more immediate release coatings, protective coatings, enteric or delayed release coatings, sustained release coatings, barrier coatings, and combinations thereof. In some embodiments, an immediate release coating may be used to improve product elegance as well as for a moisture barrier, and taste and odor masking. Rapid breakdown of the film in gastric media is important, leading to effective disintegration and dissolution.

Capsular materials (i.e., the activated fatty acid containing core and/or one or more coating layers) may further include one or more preservatives, coloring and opacifying agents, flavorings and sweeteners, sugars, gastroresistant substances, or combinations thereof. Suitable preservative and colorant are known in the art and include, for example, benzoic acid, para-oxybenzoate, caramel colorant, gardenia colorant, carotene colorant, tar colorant, and the like. In particular embodiments, one or more flavoring agents may be included the contents of the core of the gelatin capsule or in one or more coating layers of the capsule, or a combination thereof. For example, providing a palatable flavoring to the activated fatty acid gel capsule may be achieved by providing a flavored coating layer having a water soluble flavor. In such embodiments, from about 0.25% and about 1.50% by weight of said coating layer may be the water soluble flavoring. Any suitable flavor known in the art may be provided to the coating layer, such as, berry, strawberry, chocolate, cocoa, vanilla, lemon, nut, almond, cashew, macadamia nut, coconut, blueberry, blackberry, raspberry, peach, lemon, lime, mint, peppermint, orange, banana, chili pepper, pepper, cinnamon, and/or pineapple. In some embodiments, an oil soluble flavoring may be mixed with an activated fatty acid core that is encapsulated within the capsule. In such embodiments, from about 0.25% and about 1.50% by weight of said core may be the oil soluble flavoring. Such oil soluble flavoring may be similar to the taste of the flavor of the capsule, e.g., strawberry and strawberry, or the taste of the oil flavoring may be complementary to the capsule flavoring, e.g., banana and strawberry. Such flavoring agents and methods for providing flavoring to fatty acid containing capsules may be found in U.S. Pat. Nos. 6,346,231 and 6,652,879 which are hereby incorporated by reference in their entireties.

In some embodiments, the gel capsules of embodiments may include at least one coating layer including one or more secondary agent. In such embodiments, a layer including one or more secondary agent may be of sufficient thickness to prevent oxidative degradation of the one or more secondary agent. For example, in some embodiments, the thickness of this layer may be from about 5 to about 400 microns, about 10 to about 200 microns, about 20 to about 100 microns, or in certain embodiments, from about 40 to about 80 microns. In other embodiments, the thickness of such layers may be expressed in terms of percentage weight gain based on the total weight of the capsule. For example, a layer including one or more secondary agents may create a weight gain of about 0.05 to about 20%, about 0.1 to about 10%, about 0.1 to about 5%, and in particular embodiments about 0.25 to about 1%. In certain embodiments, a coating layer containing one or more secondary agent may further include at least one compound to prevent oxidative degradation. For example, in some embodiments, at least one polymer, such as, but not limited to cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions, and combinations thereof, preferably hydroxypropyl cellulose, ethyl cellulose, and mixtures thereof, may be added to the coating layer at a ratio of polymer to secondary agent of from about 1:20 to about 20:1 by weight or about 1:5 to about 10:1 by weight. In particular, where the amount of secondary agent is less than about 15 mg, the amount of polymer may be from about 1:2 to about 5:1 or from about 1:1 to about 4:1, and in embodiments where the amount of secondary agent is about 15 mg or more, the amount of polymer may be from about 1:4 to about 4:1 or about 1:3 to about 2:1.

In embodiments in which one or more secondary agents are applied in a coating layer, the secondary agent may be provided as a homogenous coating solution or a heterologous suspension in a pharmaceutically acceptable solvent. Such pharmaceutically acceptable solvents may be an aqueous or organic solvent such as, for example, methanol, ethanol, isopropranol, ethylene glycol, acetone, or mixtures thereof. In other embodiments, pharmaceutically acceptable solvents may include, but are not limited to, polypropylene glycol, polypropylene glycol, polyethylene glycol, for example, polyethylene glycol 600, polyethylene glycol 900, polyethylene glycol 540, polyethylene glycol 1450, polyethylene glycol 6000, polyethylene glycol 8000, and the like; pharmaceutically acceptable alcohols that are liquids at about room temperature, for example, propylene glycol, ethanol, 2-(2-ethoxyethoxy)ethanol, benzyl alcohol, glycerol, polyethylene glycol 200, polyethylene glycol 300, polyethylene glycol 400 and the like, polyoxyethylene castor oil derivatives, for example, polyoxyethyleneglycerol triricinoleate or polyoxyl 35 castor oil, polyoxyethyleneglycerol oxystearate, RH 40 (polyethyleneglycol 40 hydrogenated castor oil) or RH 60 (polyethyleneglycol 60 hydrogenated castor oil), and the like, saturated polyglycolized glycerides; polyoxyethylene alkyl ethers, for example, cetomacrogol 1000 and the like; polyoxyethylene stearates, for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like; ethyl oleate, isopropyl palmitate, isopropyl myristate and the like; dimethyl isosorbide; N-methylpyrrolidinone; parafin; cholesterol; lecithin; suppository bases; pharmaceutically acceptable waxes, for example, carnauba wax, yellow wax, white wax, microcrystalline wax, emulsifying wax and the like; pharmaceutically acceptable silicon fluids; soribitan fatty acid esters such as sorbitan laurate, sorbitan oleate, sorbitan palmitate, sorbitan stearate and the like; pharmaceutically acceptable saturated fats or pharmaceutically acceptable saturated oils, for example, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate and the like.

Any method for preparing gel capsules known in the art may by used in various embodiments of the invention. For example, in one embodiment, capsules may be produced by a method including the steps of preparing a sheet of an outer coating layer and one or more sheets of other layers, laminating the sheets, drying the laminated sheets to obtain a dried sheet, and encapsulating one or more activated fatty acid or one or more activated fatty acids and one or more secondary agents within the dried sheet on a rotary filler to form a seamed capsule. In another embodiment, seamless capsules may be produced using an instrument equipped with two or more nozzles arranged concentrically. In other embodiments, gelatin capsules may be manufactured as, for example, a two-piece, sealed or unsealed hard gelatin capsule.

In another embodiment, a gelatin capsule including nitro fatty acids may be formed by the encapsulation of a dose of one or more nitro fatty acid in a gelatin capsule. In such embodiments, the gelatin capsule may be made of, for example, gelatin, glycerol, water, a flavoring, a coloring agent and combinations thereof, and the nitro fatty acid dose may be, for example, 180 mg of nitrated EPA and 120 mg of nitrated DHA. The manufacturing process of such embodiments may include the steps of combining gelswatch ingredients, melting and forming a liquefied gelswatch, delivering the liquefied gelswatch and the nitro fatty acid to an encapsulation machine, encapsulating a dose of nitro fatty acid, drying the encapsulated dose, washing the encapsulated dose and packaging the nitro fatty acid capsules for shipment. The gelswatch ingredients may include any ingredients described herein that are useful in the production of gelatin capsules such as, for example, gelatin or a gelatin substitute such as modified starch or other suitable gelatin substitute known in the art, a softener such as glycerol or sorbitol or other suitable polyol or other gelatin softener known in the art, a flavoring agent such as strawberry flavor Firmenich #52311A or other suitable gelatin capsule flavoring known in the art and optionally a coloring agent such as keratin or other suitable gelatin capsule coloring agent known in the art.

In particular embodiments, the gel capsule may be formed from a gelswatch mixture of about 45 parts by weight of gelatin, about 20 parts by weight of glycerol, about 35 parts by weight of water and about 0.5 or more parts by weight of flavoring. The gelswatch ingredients may be heated to about 60° C. to 70° C. and mixed together to form liquefied gelswatch. The liquefied gelswatch and the nitro fatty acid may then be poured into an encapsulation machine. The encapsulation machine then forms the nitro fatty acid capsule by encapsulating the nitro fatty acid dose into a gelatin capsule.

The capsule can then be dried at a temperature of, for example, about 20° C. The water content of the capsule may be reduced by evaporation during the drying step. The capsule can then be washed and ready for packaging, selling, or shipping. In some embodiments, a sweetener or flavoring agent can be added to the capsule through a dipping process. In the dipping process, the gelatin capsule is dipped in a sweetener/flavoring solution and then dried, allowing for the sweetener to form a coating around the outside of the capsule. In some embodiments, a sweetener or flavoring agent may be added to the capsule through an enteric coating process, and in other embodiments, a liquefied sweetener or flavoring agent can be sprayed on to the outside of the gelatin capsule and dried. Other methods of making gelatin capsules are known in the art and contemplated.

In various embodiments, the one or more coatings on the capsule may be applied by any technique known in the art including, but not limited to, pan coating, fluid bed coating or spray coating, and the one or more coatings may be applied, for example, as a solution, suspension, spray, dust or powder. For example, in some embodiments, a polymeric coating may be applied as aqueous-based solutions, organic-based solutions or dispersions containing and, in some embodiments, one or more secondary agent. In such embodiments, polymer-containing droplets may atomized with air or an inert gas and sprayed onto the a core containing the activated fatty acids, and in some embodiments, heated air or inert gas may be added to facilitate evaporation of the solvent and film formation. In the case of soft gelatin capsules, the processing parameters of spray rate and bed temperature must be controlled to limit solubilization and capsule agglomeration. Additionally, a high bed temperature may result in evaporation of residual water from the capsule shell, causing the capsule to become brittle. In addition, coating uniformity which includes mass variance of the coated capsules and variance of the content of the coated activated fatty acid and accuracy of deposition must be evaluated.

Gel capsules of various embodiments of the invention may be of any shape such as, but not limited to, round, oval, tubular, oblong, twist off, or a non-standard shape (e.g., animal, tree, star, heart, etc.), and the size of the capsule may vary in accordance to the volume of the fill composition intended to be contained therein. For example, in some embodiments, hard or soft gelatin capsules may be manufactured using conventional methods as a single body unit comprising the standard capsule shape. A single-body soft gelatin capsule typically may be provided, for example, in sizes from 3 to 22 minims (1 minim=0.0616 ml) and in shapes of oval, oblong or others. Similarly, hard gel capsules may be manufactured using conventional methods in standard shapes and various standard sizes, such as those designated (000), (00), (0), (1), (2), (3), (4), and (5) where the largest number corresponds to the smallest size. Non-standard shapes may be used as well.

Other pharmaceutical formulations containing the compounds of the invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of an activated fatty acid in solid dosage form may vary. For example, in one embodiment, a liquid or gelatin formulation of the activated fatty acid may be prepared by combining the activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an activated fatty acid prepared as described above may be lyophilized to for a solid that may be mixed with one or more pharmaceutically acceptable excipient, carrier or diluent to form a tablet, and in yet another embodiment, the activated fatty acid of an oily preparation may be crystallized to from a solid which may be combined with a pharmaceutically acceptable excipient, carrier or diluent to form a tablet.

Further embodiments which may be useful for oral administration of activated fatty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids may have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated.

Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates:

Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include activated fatty acids administered in combination with other active such as, for example, adjuvants, protease inhibitors, or other compatible drugs or compounds where such combination is seen to be desirable or advantageous in achieving the desired effects of the methods described herein.

The activated fatty acids of various embodiments may be prepared by any method known in the art. For example, in particular embodiments, the activated fatty acids may be derived from natural sources such as, for example, fish oils and plant oils which may contain activated fatty acids, and in particular, nitro-fatty acids and keto-fatty acids, that can be isolated, purified or concentrated form the fish oil. In other embodiments, an activated fatty acid may be prepared by contacting a naturally occurring unsaturated fatty acids with one or more nitro containing compounds, nitrogenating agents, and/or oxygenating agents and the activated fatty acids may be isolated, purified, or concentrated from the resulting oils, and in some embodiments, such methods may be carried out in the presence of one or more cofactors and/or catalysts. For example, in certain embodiments, activated fatty acids may be prepared by combining an unsaturated fatty acid with one or more nitrogenating agents and/or oxygenating agents such as ammonia or primary amines, molecular oxygen and an oxidation catalyst as described in U.S. Pat. No. 4,599,430, which is hereby incorporated by reference in its entirety.

In some embodiments, the isolation, purification, or concentration of activated fatty acids may be accomplished using a variety of solid phase chromatographic strategies, which may be subjected to a gradient of solvent of increasing or decreasing polarity. In certain embodiment, an affinity based or covalent adduction strategy may be used. For example, in some exemplary embodiments, immobilized thiol-containing compounds or chromatographic beads can be used to concentrate activated fatty acids from natural or treated oils. In yet other embodiments, natural or treated oils or concentrated, isolated, or purified activated fatty acids may be additionally treated to remove harmful by-products and oxidized fatty acids.

In particular embodiments, activated fatty acids may be prepared by a method including the steps of:

a) contacting an unsaturated fatty acid with a mercuric salt and a selenium compound;

b) contacting the intermediate resulting from step a) with a reagent, enzyme, or reactant that can introduce an electron withdrawing group; and c) reacting the intermediate resulting from step b) with an oxidizing agent.

Without wishing to be bound by theory, a selenium compound, such as, for example, PhSeBr, PhSeCl, PhSeO$_2$CCF$_3$, PhSeO$_2$H, PhSeCN and the like, may react with one or more carbon-carbon double bond of the unsaturated fatty acid to form a three-membered ring intermediate on the fatty acid in a reaction that may be facilitated by the mercuric salt such as, for example, HgCl$_2$, Hg(NO$_3$)$_2$, Hg(OAc)$_2$ and the like as depicted in step I of the reaction below:

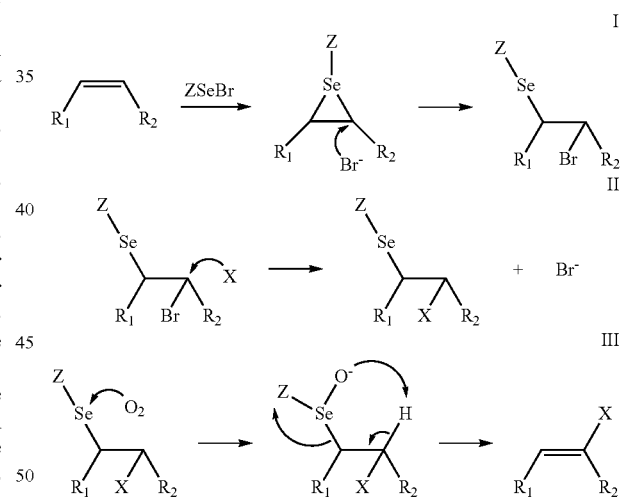

The unsaturated fatty acids may be any unsaturated fatty acid known in the art. For example, in some embodiments, the unsaturated fatty acid may be pharmaceutical or pharmaceutical composition grade fatty acids such as, for example, pharmaceutical or pharmaceutical composition grade ω-3 fatty acids. In other embodiments, the unsaturated fatty acids may be derived from fish oils which may or may not have been obtained by fractionation fish oils to concentrate the unsaturated fatty acids. In still other embodiments, the unsaturated fatty acids may be a synthetic fatty acid manufactured by any method known in the art.

The source of the electron withdrawing group may be any compound known in the art that is capable of generating an electron withdrawing group that can be incorporated into the activated fatty acid, such as, for example, NaNO$_2$, AgNO$_2$, HSO$_2$OH, and the like. Without wishing to be bound by theory, the electron withdrawing group (X in the reaction scheme above) may become joined to the hydrocarbon chain by displacing, for example, the bromine that was associated with the selenium compound as depicted in step II of the reaction scheme provided above. It is noted that the electron withdrawing groups may also react directly with the three-membered ring episelenonium ion shown in step I at the position where the bromine is shown as attacking Finally, as depicted in step III of the reaction scheme provided above, the oxidizing agent forms a reactive selenium-oxo functional group which undergo molecular rearrangement and elimination of ZSeOH leading to formation of the electron withdrawing vinyl (depicted as a nitro vinyl) on the hydrocarbon chain. Z in the reaction scheme above may be any number of groups. For example, in certain embodiments, Z may be a phenyl group.

In other embodiments, an activated fatty acid may be prepared using a modified aldol condensation such as the Henry reaction. A review of the Henry reaction and methods related to the Henry method can be found, for example, in Frederick A. Luzzio, F. A. "The Henry reaction: recent examples" Tetrahedron 2001, 57, 915-945 which is hereby incorporated by reference in its entirety. Known variations of the Henry reaction may also be useful in preparing activated fatty acids and all such methods are embodied herein. For example, in some embodiments, variations of the Henry reaction including, but not limited to, the Wittig-like variation of the Henry reaction, the Horner-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Horner-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Horner-Wittig, Horner-Wadsworth-Emmons can be found, for example, in Peterson, Johnson, and Julia reactions. Blakemore, P. R. "The modified Julia olefination: alkene synthesis via the condensation of metallated heteroarylalkylsulfones with carbonyl compounds *J. Chem. Soc., Perkin Trans.* 1, 2002, 2563-2585 which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitroaldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitro-octadec-9-enoic Acids" *Organic Letters,* 2006, 8, 3931-3934 which provides one regioisomer and usually one of two possible alkene cis/trans or Z/E diastereomers, in high purity and usually in high chemical yield, which is hereby incorporated by reference in its entireties.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N. C. "Catalytic Asymmetric Henry Reaction" *Tetrahedron: Asymmetry* 2006, 17, 3315-3326 which is hereby incorporated by reference in its entirety, describes methods for preparing stereospecific isomers of nitoralkenes.

In still other embodiments, alkenes (olefins) may be prepared by metal-mediated cross coupling reactions (joining together of two molecules to make one new molecule) by condensation onto a carbonyl compound. Such methods have not been applied to the formation of nitroalkenes or to the formation of other alkenes with electron-withdrawing substituents, but such methods could be adapted to the synthesis of alkenes with electron-withdrawing substituents. For example, named cross coupling reactions such as the Heck, Suzuki and Stille coupling, along with others may be used to prepare activated fatty acids. Such methods are well known in the art. A review of such reactions of can be found in, for example, Metal-Catalyzed Cross-Coupling Reactions de Meijere, Armin/Diederich, Francois (eds.) Wiley-VCH, Weinheim 2004. XXII, ISBN-10: 3-527-30518-1 and ISBN-13: 978-3-527-30518-6 which are hereby incorporated by reference in their entireties.

Examples of various embodiments of methods for preparing activated fatty acids may at least include the following steps:

i) combining a first component at least including an aliphatic hydrocarbon having an electron withdrawing group at one end with an second component including aliphatic hydrocarbon chain having an aldehyde at one end in the presence of a base to form a first intermediate; and ii) generating an alkene from the first intermediate.

Exemplary reactions are presented in schemes I and II below:

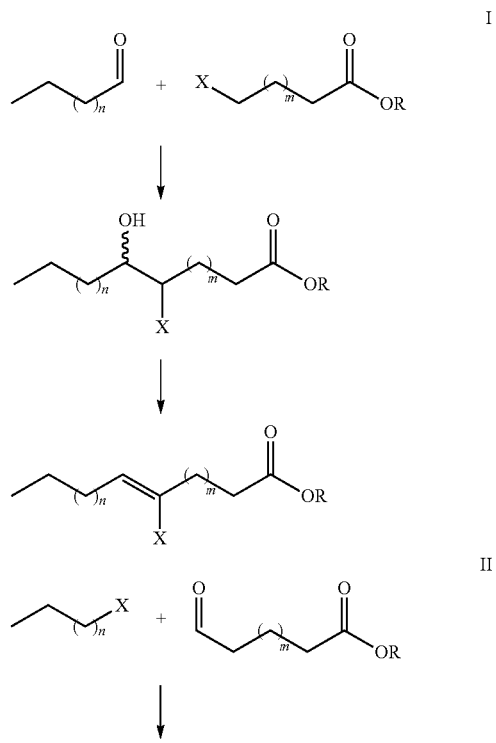

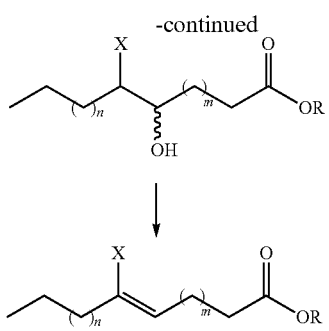

In reaction schemes I and II, the variable X represents an electron withdrawing group and can be any electron withdrawing group discussed herein above or known in the art. The variables n and m represent a number of carbon atoms in the aliphatic hydrocarbon chain, and n and m can be any number. For example, the aliphatic hydrocarbon chains of any of the starting compound may be from 2-20 carbons in length. Moreover, the position of the double bond and the arrangement of the electron withdrawing group in relation to the double bond may be determined specifically, and particular activated fatty acids may be created in high yield. For example, an oleic acid may be produced by the reaction of scheme I by combining a first substrate where m is 10 and a second substrate where n is 2.

Various embodiments of the invention are also directed to method for administering activated fatty acids. Specific modes of administration may vary and may depend on the indication. The selection of the specific route of administration and the dose regimen may be adjusted or titrated according to known methods in order to obtain the optimal response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art. Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Example 1

B6129S2/J mice (male, 3-4-mo-old) received vehicle (saline) or a single i.p. (intraperitoneal) injection of cisplatin alone (20 mg/kg in saline). After 20 minutes, the cisplatin group was randomly divided to receive an i.p injection of OA-NO$_2$ (400 mg/kg in ethanol) or an equivalent amount of ethanol at 6-hour intervals for 48 hours. The control group also received an i.p. injection of the equivalent amount of ethanol at the same frequencies. At the end of the experiments, under isoflurane anesthesia, blood was withdrawn from the vena cava using 1 cc insulin syringe and kidneys were harvested for analysis of morphology and gene expression.

A single i.p. injection of cisplatin induced renal dysfunction as indicated by a rise in plasma BUN, renal histological abnormalities characterized by distortion of the overall renal morphology, dilation of renal tubules, and appearance of protein cast. In a sharp contrast, posttreatment with OA-NO$_2$ markedly attenuated these functional and pathological changes. In addition, cisplatin treatment induced increased MPO plasma level (marker of neutrophil infiltration), kidney expression of NADPH oxidase subunits p47$^{phox}$ and gp91$^{phox}$ (major superoxide generating enzyme), kidney thiobarbituric acid-reactive substances (TBARS, index of oxidative stress), and activity of caspase (index of apoptosis), all of which were attenuated or completely corrected by OA-NO$_2$.

Example 2

In cultured human proximal tubular cells (HK2), exposure to 1.0 μM cisplatin induced a 3-fold increase in caspase activity that was almost completely normalized by OA-NO$_2$ Example 3

B6129S2/J mice (male, 3-4-mo-old) will receive vehicle (saline) or a single i.p. (intraperitoneal) injection of diatrizoic acid (20 mg/kg in saline). After 20 minutes, the diatrizoic acid group will be randomly divided to receive an i.p injection of OA-NO$_2$ (400 mg/kg in ethanol) or an equivalent amount of ethanol at 6-hour intervals for 48 hours. The control group will also receive an i.p. injection of the equivalent amount of ethanol at the same frequencies. At the end of the experiments, under isoflurane anesthesia, blood will be withdrawn from the vena cava using 1 cc insulin syringe and kidneys will be harvested for analysis of morphology and gene expression.

A single i.p. injection of diatrizoic acid is expected to induce renal dysfunction as indicated by a rise in plasma BUN, renal histological abnormalities characterized by distortion of the overall renal morphology, dilation of renal tubules, and appearance of protein cast. In a contrast, posttreatment with OA-NO$_2$ should attenuated these functional and pathological changes and reduce vasoconstriction associated with these characteristics.

The invention claimed is:

1. A method for treating contrast agent-induced nephropathy in a subject comprising administering a therapeutically effective amount of an activated fatty acid, a prodrug, or a metabolite thereof, wherein the activated fatty acid is an unsaturated or polyunsaturated fatty acid having an aliphatic chain comprised of 4 to 25 carbons and one or more electron withdrawing groups associated with at least one carbon-carbon double bond, the one or more electron withdrawing groups being selected from the group consisting of aldehyde (—COH), acyl (—COR), carbonyl (—CO), carboxylic acid (—COOR), ester (—COOR), halides (—Cl, —F, —Br, —I), fluoromethyl (—CFn, n=I-3), allyl fluoride (—CH═CHCH2F), cyano (—CN), sulfoxide (—SOR), sulfonyl (—S02R), sulfonic acid (—S03H), 1°, 2° and 3° ammonium (—NR3 +), or nitro (—N02), wherein R is a hydrogen, methyl or C2-C6 alkyl, further comprising administering one or more secondary agents selected from the group consisting of cytoprotective agents, angiotensin II inhibitors, angiotensin converting enzyme (ACE) inhibitors, and combinations thereof.

2. The method of claim 1, wherein the activated fatty acids selected from the group consisting of nitro-linoleic acid, keto-linoleic acid, nitro-oleic acid, and keto-oleic acid.

3. The method of claim 1, wherein the activated fatty acid is nitro-oleic acid.

4. The method of claim 1, further comprising administering a contrast agent.

5. The method of claim 1, further comprising the step of administering a contrast agent before administration of the activated fatty acid, simultaneously with the activated fatty acid, after administration of the activated fatty acid, or combinations thereof.

6. The method of claim 4, wherein the contrast agent being administered is selected from the group consisting of diatrizoic acid, iopamidol, iodixanol, iohexol, ioxaglic acid, ioversol, iopromide, iothalamic acid, and combinations thereof.

7. The method of claim 1, further comprising administering one or more secondary agents selected from the group consisting amifostine, 2-mercapto ethane sulfonate sodium, and combinations thereof concurrently or within the same course of treatment with the activated fatty acid.

8. The method of claim 1, further comprising administering one or more secondary agents selected from the group consisting irbesartan, losartan, ramipril, enalapril, lisinopril, quinapril, benazepril, captopril, fosinopril, trandolapril, moexipril, perindopril, and combinations thereof concurrently or within the same course of treatment with the activated fatty acid.

9. The method of claim 1, wherein the activated fatty acid is contained in a pharmaceutical composition comprising:
the one or more activated fatty acids; and
a pharmaceutically acceptable diluent, carrier, excipient, or combination thereof.

10. The method of claim 9, wherein the pharmaceutical composition further comprises a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof.

11. The method of claim 1, wherein the nephropathy comprises hypercalcemia, hyperuricemia, lysozymuria, disseminated intravascular coagulopathy, immune complex-mediated glomerulopathy, paraprotein-related nephropathy, amyloidosis, and urinary tract infections, or any combinations thereof.

12. The method of claim 1, further comprising the step of attenuating at least one of MPO plasma level, kidney expression of NADPH oxidase subunits $p47^{phox}$ and $gp91^{phox}$, kidney thiobarbituric acid-reactive substances, and caspase activity in the subject.

13. The method of claim 3, further comprising the step of attenuating at least one of MPO plasma level, kidney expression of NADPH oxidase subunits $p47^{phox}$ and $gp91^{phox}$, kidney thiobarbituric acid-reactive substances, and caspase activity in the subject.

14. The method of claim 1, wherein the electron withdrawing group is positioned on one of an alpha carbon, beta carbon or gamma carbon of a carbon-carbon double bond in the aliphatic chain.

15. A method for treating contrast agent-induced nephropathy in a subject comprising administering a therapeutically effective amount of an activated fatty acid, a prodrug, or a metabolite thereof, wherein the activated fatty acid is an unsaturated or polyunsaturated fatty acid having an aliphatic chain comprised of 4 to 25 carbons and one or more electron withdrawing groups associated with at least one carbon-carbon double bond, the one or more electron withdrawing groups being selected from the group consisting of aldehyde (—COH), acyl (—COR), carbonyl (—CO), carboxylic acid (—COOR), ester (—COOR), halides (—Cl, —F, —Br, —I), fluoromethyl (—CFn, n=1-3), allyl fluoride (—CH=CHCH2F), cyano (—CN), sulfoxide (—SOR), sulfonyl (—SO2R), sulfonic acid (—SO3H), 1°, 2° and 3° ammonium (—NR3+), or nitro (—NO2), wherein R is a hydrogen, methyl or C2-C6 alkyl, wherein the nephropathy comprises hypercalcemia, hyperuricemia, lysozymuria, disseminated intravascular coagulopathy, immune complex mediated glomerulopathy, paraprotein-related nephropathy, amyloidosis, and urinary tract infections, or any combinations thereof.

16. The method of claim 15, wherein the activated fatty acids selected from the group consisting of nitro-linoleic acid, keto-linoleic acid, nitro-oleic acid, and keto-oleic acid.

17. The method of claim 15, wherein the activated fatty acid is nitro-oleic acid.

18. The method of claim 15, further comprising administering a contrast agent.

19. The method of claim 15, further comprising the step of administering a contrast agent before administration of the activated fatty acid, simultaneously with the activated fatty acid, after administration of the activated fatty acid, or combinations thereof.

20. The method of claim 18, wherein the contrast agent being administered is selected from the group consisting of diatrizoic acid, iopamidol, iodixanol, iohexol, ioxaglic acid, ioversol, iopromide, iothalamic acid, and combinations thereof.

21. The method of claim 15, further comprising administering one or more secondary agents selected from the group consisting of cytoprotective agents, angiotensin II inhibitors, angiotensin converting enzyme (ACE) inhibitors, and combinations thereof.

22. The method of claim 15, further comprising administering one or more secondary agents selected from the group consisting amifostine, 2-mercapto ethane sulfonate sodium and combinations thereof concurrently or within the same course of treatment with the activated fatty acid.

23. The method of claim 15, further comprising administering one or more secondary agents selected from the group consisting irbesartan, losartan, ramipril, enalapril, Lisinopril, quinapril, benazepril, captopril, fosinopril, trandolapril, moexipril, perindopril and combinations thereof concurrently or within the same course of treatment with the activated fatty acid.

24. The method of claim 15, wherein the activated fatty acid is contained in a pharmaceutical composition comprising:
the one or more activated fatty acids; and
a pharmaceutically acceptable diluent, carrier, excipient, or combination thereof.

25. The method of claim 24, wherein the pharmaceutical composition further comprises a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof.

26. The method of claim 15, further comprising the step of attenuating at least one of MPO plasma level, kidney expression of NADPH oxidase subunits p47phox and gp91phox, kidney thiobarbituric acid-reactive substances, and caspase activity in the subject.

27. The method of claim 17, further comprising the step of attenuating at least one of MPO plasma level, kidney expression of NADPH oxidase subunits p47phox and gp91phox, kidney thiobarbituric acid-reactive substances, and caspase activity in the subject.

28. The method of claim 15, wherein the electron withdrawing group is positioned on one of an alpha carbon, beta carbon or gamma carbon of a carbon-carbon double bond in the aliphatic chain.

* * * * *